(12) United States Patent
Akahoshi

(10) Patent No.: US 9,233,195 B2
(45) Date of Patent: Jan. 12, 2016

(54) COMPOSITE IRRIGATION/ASPIRATION NEEDLE WITH BALL TIP

(75) Inventor: Takayuki Akahoshi, Tokyo (JP)

(73) Assignee: ART, LIMITED, Grand Cayman (KY)

( * ) Notice: Subject to any disclaimer, the term of this patent is extended or adjusted under 35 U.S.C. 154(b) by 298 days.

(21) Appl. No.: 12/566,630

(22) Filed: Sep. 24, 2009

(65) Prior Publication Data

US 2011/0015562 A1    Jan. 20, 2011

Related U.S. Application Data

(60) Provisional application No. 61/099,867, filed on Sep. 24, 2008.

(51) Int. Cl.
*A61M 1/00* (2006.01)

(52) U.S. Cl.
CPC ............. *A61M 1/008* (2013.01); *A61M 1/0058* (2013.01); *A61M 2210/0612* (2013.01)

(58) Field of Classification Search
CPC . A61M 1/0064; A61M 1/008; A61M 3/0279; A61M 3/0283; A61M 25/0068; A61M 25/0069; A61M 25/008; A61M 2210/0612; A61M 1/0058; Y10S 604/902
USPC .............. 604/93.01, 264, 272–275, 294, 521; 606/107
See application file for complete search history.

(56) References Cited

U.S. PATENT DOCUMENTS

| 4,204,328 | A  | * | 5/1980  | Kutner ........................... 433/29 |
| 4,531,943 | A  | * | 7/1985  | Van Tassel et al. ........... 604/523 |
| 5,836,926 | A  | * | 11/1998 | Peterson et al. .............. 604/527 |
| 6,159,175 | A  | * | 12/2000 | Strukel et al. .................. 604/22 |
| 6,491,670 | B1 | * | 12/2002 | Toth et al. ..................... 604/264 |
| 6,494,868 | B2 | * | 12/2002 | Amar ............................. 604/273 |
| 2004/0267211 | A1 | * | 12/2004 | Akahoshi ..................... 604/264 |

* cited by examiner

*Primary Examiner* — Kami A Bosworth
(74) *Attorney, Agent, or Firm* — Wood, Phillips, Katz, Clark & Mortimer

(57) ABSTRACT

An irrigation/aspiration needle has a rigid needle body over which an elastomeric sleeve is fitted. The elastomeric sleeve terminates in a smooth, relatively soft, rounded tip through which a passageway extends, communicating with a passageway in the sleeve which, in turn, communicates with passageways in the needle body and needle mount, forming a liquid flow path through the needle. The softness of the elastomeric sleeve and, particularly, the sleeve tip protects delicate eye tissue when the needle is used for aspiration from or irrigation of the eye during surgery.

13 Claims, 4 Drawing Sheets

COMPOSITE IRRIGATION/ASPIRATION NEEDLE WITH BALL TIP

PRIORITY

This application claims priority from U.S. Provisional Patent Application Ser. No. 61/099,867, filed 24 Sep. 2008, which is incorporated herein in its entirety by reference.

FIELD OF THE INVENTION

The present invention relates to instruments used in eye surgery and, more particularly, to an irrigation/aspiration (I/A) needle used to remove particles from the capsular bag after removal of a lens.

BACKGROUND AND SUMMARY OF THE INVENTION

The lens of a human eye is held within a capsular bag positioned behind the iris in the anterior chamber of the eye. When the lens becomes damaged or diseased a common surgical technique is to remove the lens and replace it with an artificial intraocular lens (IOL). Removal of the lens is commonly carried out by phacoemulsification, that is, using a needle to which vibrational electrical energy is transmitted by a phacoemulsification hand piece.

During phacoemulsification, the lens is broken into fragments and the fragments are emulsified and then removed from the capsular bag by aspirating the fragments through a cannula formed as part of the phacoemulsification needle. After the lens has been removed, the capsular bag must be cleaned in order to prepare it for the insertion of an IOL. In particular, epithelial and cortical tissue fragments must be removed from the floor and perimeter of the capsular bag.

Complete removal of the cortex is important for several reasons. If the cortex is not completely removed it may cause post-operative inflammation and an increase in intraocular pressure. Incomplete removal of the cortex may also cause decentration or tilting of the IOL which, in turn, would cause a postoperative refractive error or induced astigmatism. This is especially important if the IOL is a multi-focal type. Incomplete removal of the cortex may also result in the formation of another cataract which would impair vision.

The present invention has a relatively soft exterior cover which terminates in a substantially spherical tip larger in diameter than the needle. The ball-like, or rounded shape of the tip presents a softer surface with no angles to lessen the possibility of injury to the cortex. The tip can be used to polish the anterior capsule to remove fine cortical residue as well as any remaining viscoelastic material present after implanting the lens. To aspirate the viscoelastic material, the tip is introduced beneath the IOL accomplishing aspiration without stressing the capsular bag or the ciliary zonules.

It is common to use an I/A needle which is straight along its entire length in order to effect removal of the tissue fragments. This requires movement of the needle across the floor and around the periphery of the capsular bag, a range of motion to which the straight needle is not particularly well-suited. The prior art demonstrates attempts to solve this problem by using curved or curvable needles which attempt to improve maneuverability within the eye during surgery.

It is also known to provide straight needles with round or rounded tips formed from hard, metallic material, and to place the aspiration port at an angle to the needle's central passage to provide increased maneuverability.

It is also known to use a thermoplastic or compliant insert with a metallic needle and to have the insert terminate in a ball-like or bulbous shape with an aspiration port formed therethrough. Placement of the insert on the interior of the needle reduces the cross-sectional area available for flow at the working end of the needle. The aspiration port can be angled with respect to the central needle passage by forming the metallic needle with a beveled end and inserting a compliant sleeve in the needle opening at the bevel. This arrangement leaves bare the edges surrounding the needle opening, creating possible snagging or abrasive surfaces.

U.S. Pat. No. 6,491,670 (Toth et al) teaches and describes the miniaturized surgical instruments especially useful for the opthalmologic surgical procedures and methods of making the same. Toth et al discloses an aspiration needle having an outer, rigid lumen within which a soft or "compliant" insert is placed. The insert terminates in a tip having a generally bulbous shape and through which a passage is formed that communicates with the interior passage in the hollow cannula.

U.S. Pat. No. 5,527,273 (Manna et al) teaches and describes an ultrasonic lipectomy probe and method for manufacture having a rigid shank terminating in an enlarged tip. The shank has a hollow internal passage and the tip has at least one inlet port that communicates with the internal passage of the shank. Certain of the tips have inlet ports formed at an angle to the shank passage.

U.S. Pat. No. 3,808,093 (Abraham) teaches and describes a surgical tool having an ultrasonically vibrating solid needle terminating in a curvilinear needle tip. The needle is not hollow and does not either aspirate or irrigate.

U.S. Pat. No. 4,767,404 (Renton) teaches and describes a surgical suction device having a perforated sleeve. The device includes a hollow needle terminating in a tip that has multiple vacuum ports formed therethrough, communicating with the hollow interior of the needle.

U.S. Pat. No. 5,180,363 (Idemoto et al) teaches and describes an operation device having a hollow, ultrasonically vibrated needle terminating at a tip with the tip having ports that communicate to the interior passage of the needle. Once such tip is formed in a ball-like shape and has a number of ports formed through the surface of the ball or through the surface of the tip to allow irrigating fluid or cooling fluid to pass therethrough.

U.S. Pat. No. 5,653,724 (Imonti) teaches and describes an angled phacoemulsifier tip consisting of a rigid phacoemulsification needle having a distal end which is angled with respect to the main needle body. The tip is beveled but not shaped.

U.S. Pat. No. 5,741,226 (Strukel et al) teaches and describes a phacoemulsification handpiece, sleeve and tip having a rigid ultrasonically vibrated needle terminating in a tip which has a single aspiration port formed therethrough. The tip is disclosed with various shapes including hemispherical and substantially spherical configurations.

U.S. Pat. No. 5,755,700 (Kritzinger et al) teaches and describes a corneal irrigation cannula and method of using. The cannula terminates in a tip which is larger than the diameter of the cannula and which is flattened and has multiple irrigation ports.

U.S. Pat. No. 5,993,409 (Maaskamp) teaches and describes a needle for surgical use. The needle is a phacoemulsification needle which is hollow and has a distal portion which is angled with respect to the needle body.

U.S. Pat. No. 6,126,629 (Perkins) teaches and describes a multiple port phaco needle having a hollow needle body terminating in a generally hemispherical tip and with multiple aspiration ports.

U.S. Pat. No. 6,159,175 (Strukel) teaches and describes a phaco emulsification handpiece sleeve and tip and which discloses one tip configuration which is generally hemispherical in shape and has an aspiration port formed therethrough.

U.S. Pat. No. 6,299,591 (Banko) teaches and describes a phacoemulsification handpiece and sleeve and tip which discloses a needle tip having a generally hemispherical shape and including an aspiration port.

U.S. Pat. No. 6,533,750 (Sutton et al) teaches and describes a conically shaped phaco tip. A phacoemulsification needle formed from a rigid material has a portion proximate the end of the needle that is angled with respect to the main needle body and which includes an aspiration port.

U.S. Pat. No. 7,037,296 (Kadziauskis) teaches and describes a curved multi-purpose phacoemulsification needle featuring a straight phacoemulsification needle having a rounded tip with a flat surface through which an aspiration port is formed at an angle to the axis of the needle. In one variation, the distal end of the needle is curved with respect to the main needle body.

U.S. Pat. No. 6,958,056 (Kadziauskis et al) teaches and describes teaches and describes a curved multi-purpose phacoemulsification needle featuring a straight phacoemulsification needle having a rounded tip with a flat surface through which an aspiration port is formed at an angle to the axis of the needle.

U.S. Pat. D556,322 (Akahoshi) teaches and describes a tip of a phacoemulsification needle. The tip is formed in a generally spherical shape and has a plurality of ports formed therethrough.

International Publication WO 00/74615 (Maaskamp) teaches and describes a phacoemulsification needle having a rigid hollow needle body through which multiple ports are formed proximate the tip which has a port formed therethrough.

European Patent Application EP 1,707,166 (Ghamnoun) teaches and describes an irrigation tip used with a surgical hand piece. The tip has a portion of which is curved at a single bend.

I have determined that using an outer sleeve or cover made from thermoplastic material over a metallic hollow needle results in an I/A instrument that presents a smooth tip surface for polishing the cortex and also allows the tip to have a port formed therethrough which communicates with the hollow passageway in the metallic needle via a tip passageway. The tip port can be placed at any desired location on the tip and the tip passageway is then extended to meet the needle passageway at an angle.

I have also determined that needles so designed can have straight or curved configurations to allow for selectable maneuverability in use.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

Reference will hereinafter be made to the accompanying drawings which illustrate aspects of the invention and prior art though not necessarily to scale, where like reference numerals used in the various figures denote like structural elements, and wherein.

DETAILED DESCRIPTION OF THE DRAWINGS

Figure 1:
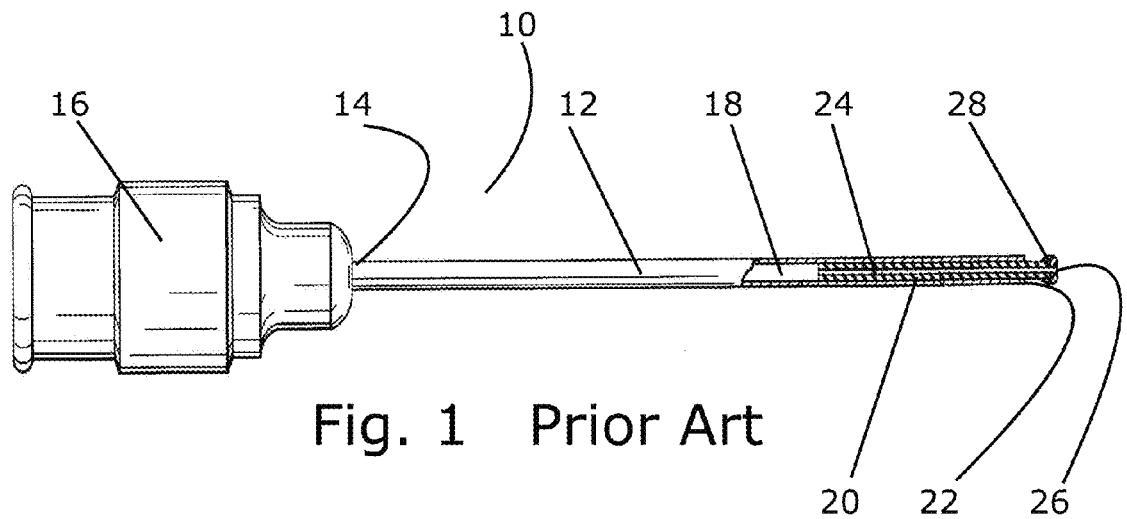
FIG. 1 is a partial side sectional view of a prior art irrigation needle.

Referring now to FIG. 1, numeral 10 identifies a miniaturized surgical instrument as described in U.S. Pat. No. 6,491,670. Instrument 10 has a rigid stainless steel tubular needle 12 having a proximal end 14 to which a needle mount 16 is attached. As seen in FIG. 1, needle 12 has a central passageway 18 extending therethrough. A flexible tube section 20 formed of an elastomeric material is inserted into needle 12 at distal needle end 22. Tube section 20 has a central passageway 22 formed therethrough communicating with needle passageway 18 at one end thereof, and at the other end thereof tube section 20 has a discharge port 26 formed in and defined by a bulbous shaped tip 28. As can be seen in FIG. 1, tube section passageway 24 is smaller in diameter than needle passageway 18.

Figure 2:
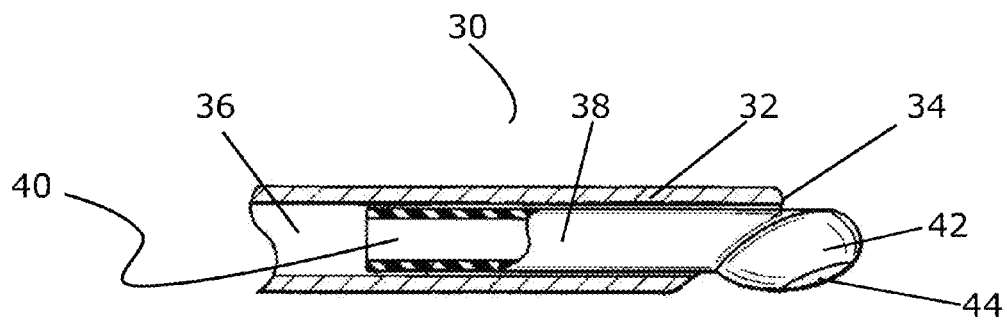
FIG. 2 is another view of the needle shown in FIG. 1.

Referring now to FIG. 2, numeral 30 identifies a second embodiment of the surgical instrument described in U.S. Pat. No. 6,491,670. Needle instrument 30 has a rigid needle body 32 terminating at a beveled tip 34. In the embodiment shown, needle body 32 has a hollow central passageway 36 extending therethrough.

An elastomeric tube section 38 is inserted into needle body 32 at tip 34 and has a tube section passageway 40 extending therethrough and communicating with needle passageway 36. Tube section 38 terminates at a tip 42 which, in this embodiment, is shown formed at an angle to tube section 38 and which has an open discharge port 44 which communicates with section passageway 40. As seen in FIG. 2, tube section passageway 40 is smaller in diameter than needle passageway 36.

Figure 3:
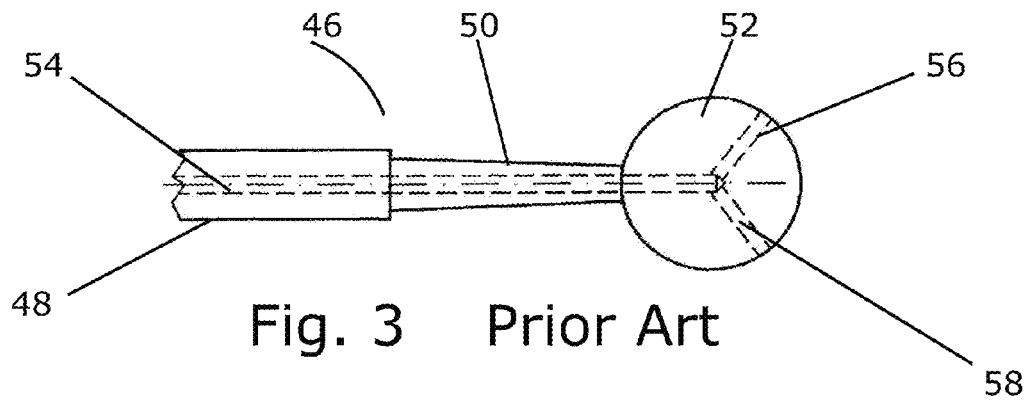
FIG. 3 is a partial side elevational view of a prior art irrigation tip.

Referring now to FIG. 3, the numeral 46 identifies a prior art lipectomy instrument as shown and described in U.S. Pat. No. 5,527,273. Lipectomy probe 46 has a rigid hollow straight shank section 48 attached to a rigid or hollow tapered shank section 50 and terminating in a rigid spherical tip 52. Probe 46 has a central passageway 54 formed therethrough and extending through shank sections 48 and 50 and tip 52. In the embodiment shown, tip 52 has a pair of angled passageways 56, 58 formed therethrough and communicating with central passageway 54.

Figure 4:
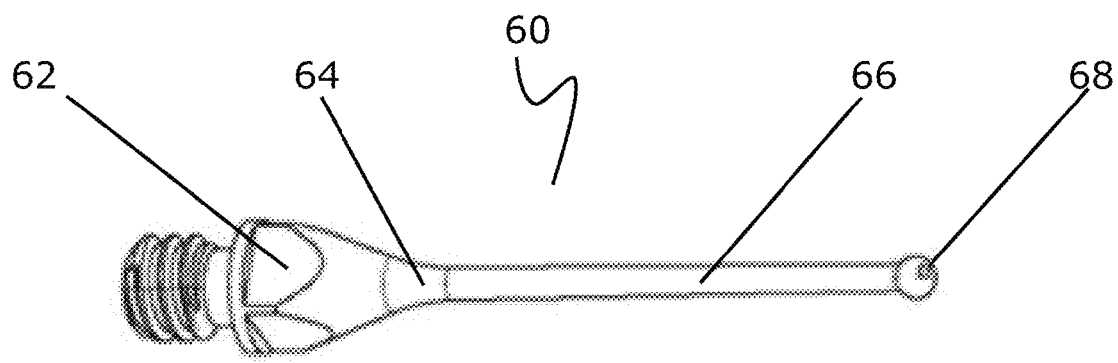
FIG. 4 is a side perspective view of an irrigation/aspiration needle embodying certain principles of the present invention.

Referring now to FIG. 4, the numeral 60 identifies generally an irrigation aspiration needle constructed in accordance with certain principles of the present invention. Needle 60 has a mount 62 from which extends a hollow, rigid needle body 64. An elastomeric needle sheath or sleeve 66 extends about the outer periphery of needle body 64 and terminates in a sleeve tip 68. Needle body 64 is represented in the prior art by I/A needles having straight needle cannulas and are available for use in such a configuration.

Figure 5:
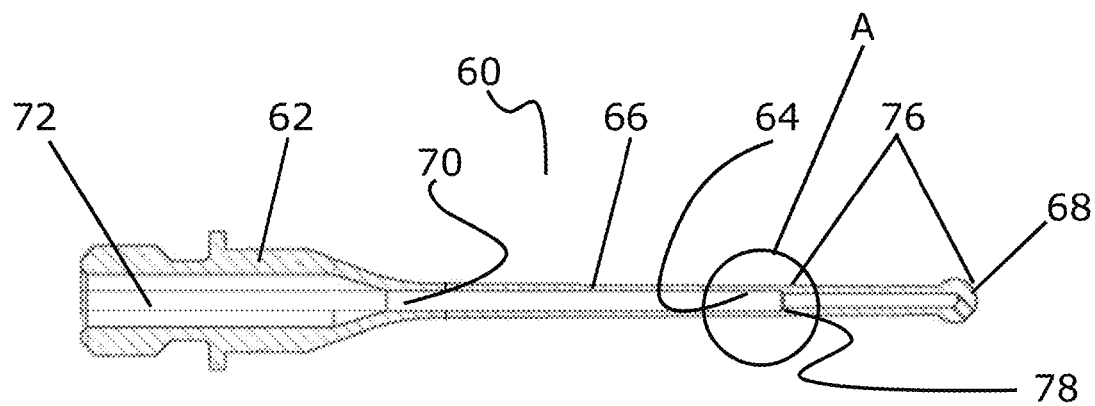
FIG. 5 is a lateral sectional view of the needle of FIG. 4.

Referring now to FIG. 5, a sectional view of the instrument shown in FIG. 4 is presented illustrating the presence of a central needle shaft passageway 70 extending through needle body 64 and communicating with a central mount passageway 72. In like fashion, sleeve 66 has a central passageway 74 formed therethrough which communicates with tip 68 and with needle shaft passageway 70. As can be seen in FIG. 5, a sleeve portion 76 fully surrounds needke shaft end 78 and extends past needle shaft end 78 to over a majority of the length of the needle body 64. The remaining portion of sleeve 66 is in contact with and supported by needle body 64.

Sleeve 66 is preferably formed from a silicone elastomer to be substantially more flexible than the needle body 64 and have sufficient structural strength to retain the shape of tip 68 and extended section 76 during surgical procedures.

Figure 6:
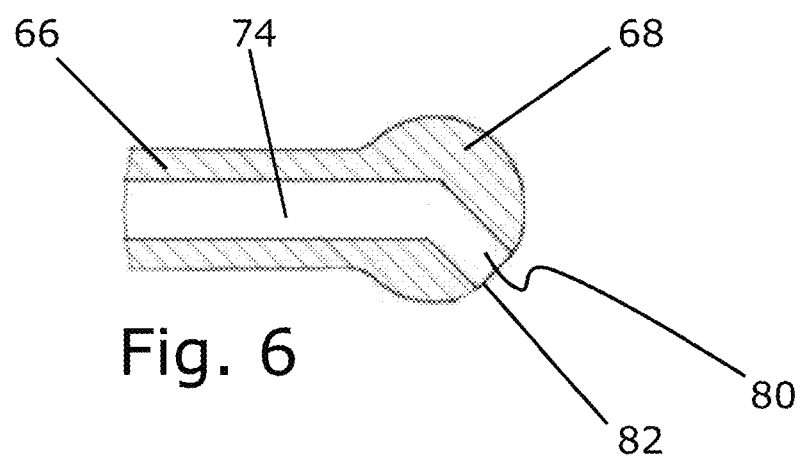
FIG. 6 is an enlarged view of the tip of FIG. 5.
Figure 5A:
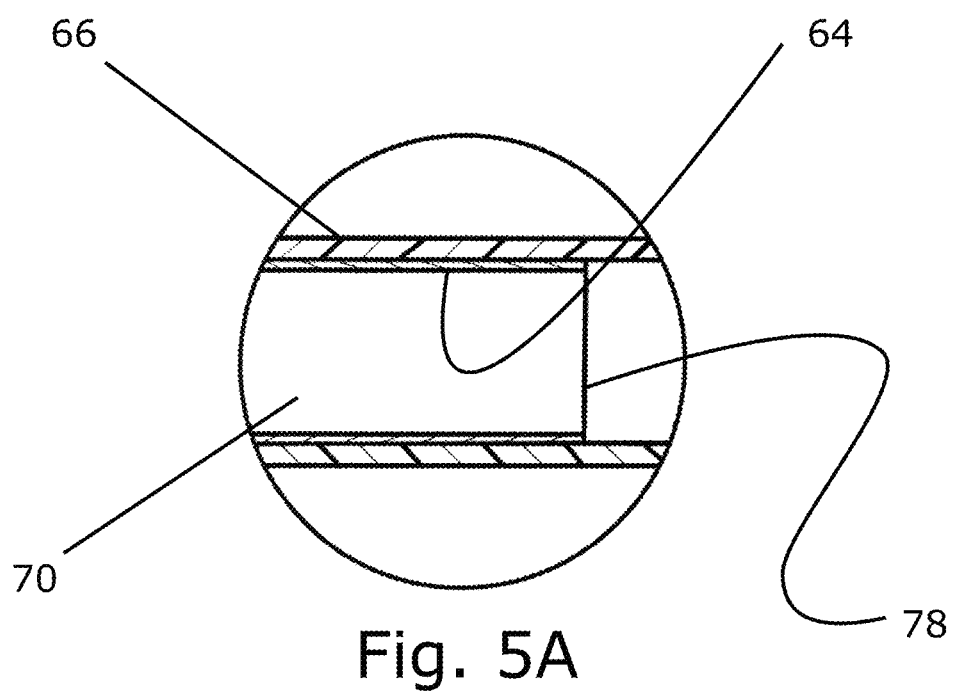
FIG. 5A is an enlarged view of detail A of FIG. 5.

Referring now to FIG. 6, an enlarged view of tip 68 of FIG. 5 is shown. As seen, tip 68 is formed in a generally rounded, substantially spherical or ball-like shape and has a tip passage 80 communicating with and extending at an angle to sleeve passage 74 and terminating at a tip port 82. The angle at which tip passageway 80 meets sleeve passageway 74 is selected to provide I/A needle 60 with a desired and desirable degree of maneuverability in order to allow tip 68 to be used to aspirate particles from the eye without removing and reorienting I/A needle 60 and without making the types of changes of position required when a straight I/A needle is used to perform the same task.

Figure 7:
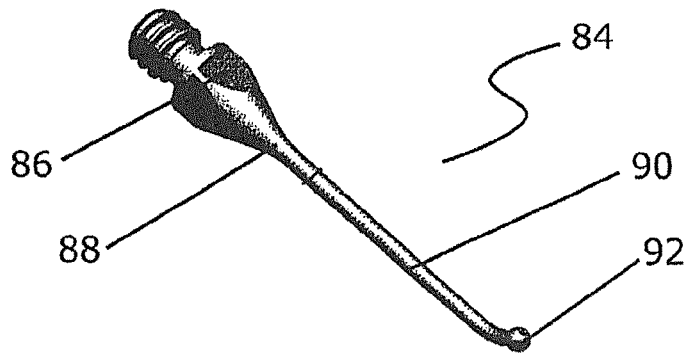
FIG. 7 is a perspective view of another embodiment of the present invention.

Referring now to FIG. 7, the numeral 84 identifies generally an irrigation/aspiration needle having a curved tip configuration embodying certain aspects of the present invention. Needle 84 extends from needle mount 86 and has a straight needle shaft 88, as described in connection with FIG. 5. A needle sleeve 90 is inserted over needle shaft 88 and terminates at needle tip 92.

Figure 8:
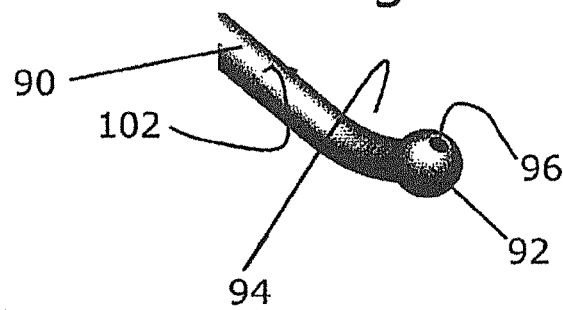
FIG. 8 is an enlarged view of the tip of FIG. 7.

Referring now to FIG. 8, the distal portion of sleeve 90 is shown having a curved portion 94 terminating at tip 92 with tip 92 having a discharge portion 96 formed thereon. As seen in FIG. 8, curved portion/bent lenght 94 extends past the terminus 102 of cannula 88.

Figure 9:
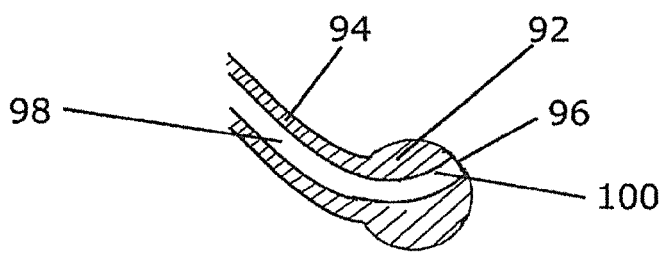
FIG. 9 is a partial side sectional view of the tip of FIG. 8.

Referring now to FIG. 9 an enlarged sectional view of tip portion 94 is shown. As seen in FIG. 9, a central passageway 98 is formed through sleeve 90 in much the same fashion as described hereinabove. Central passageway 98 extends to and is integral with curved tip passageway 100, which terminates at port 96. The center of the oassageway 100 extends in a curved path. Thus, as described hereinabove, passageways 100 and 96 communicate with a central passageway (not shown) formed in cannula 88 which, in turn, communicates with a central passageway (not shown) formed through mount 86, thus defining a flow path through irrigation/aspiration needle 84. Liquid can then travel in a path defined by port 96, passageways 100, 98 and the passageways through cannula 88 and mount 86 through needle 84. As shown in FIG. 9, tip passageway 100 meets section passageway 98 at an angle which is selected to provide a heightened degree of maneuverability to needle 84.

Needle shaft 88 may be straight throughout its length or may be curved to provide the curvature in matching section 94 of sleeve 90. Where needle 88 is straight and uncurved, it will terminate proximate curve section 94 as, for example, shown at terminus 102 in FIG. 8.

Figure 10:
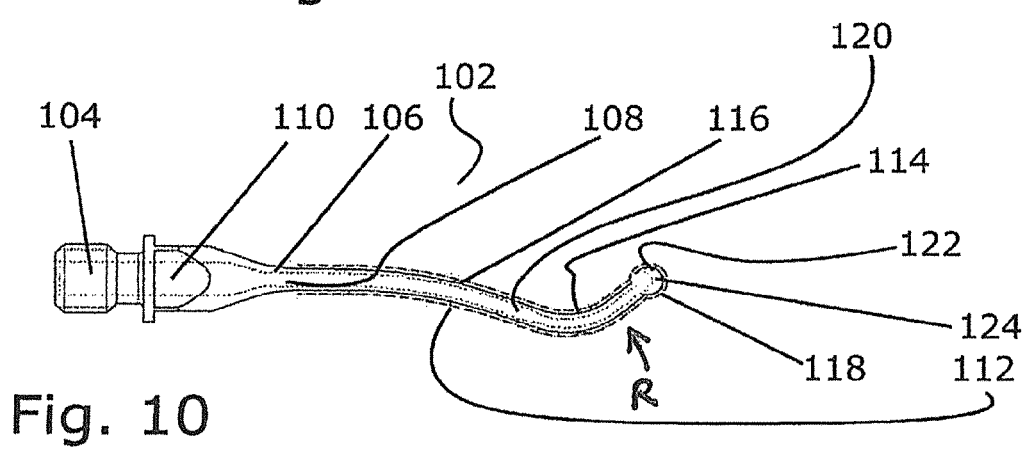
FIG. 10 is a lateral plan view of the tip shown in FIG. 7.

Referring now to FIG. 10 the numeral 102 identifies an I/A needle embodying certain aspects of the present invention. Needle 102 has a mount 104 from which a hollow, metallic needle shaft 106 extends. Needle 106 shaft has a central passageway 108 which communicates with a passageway 110 formed in mount 104. In the embodiment shown, needle shaft 106 has a first bend 112 and a second bend 114 and terminates in a region identified at R.

A portion of the outer surface of needle shaft 106 has a thermoplastic sleeve 116 thereon, terminating in a tip 118. Sleeve 116 also has a central passageway 120 communicating with a tip passageway 122 and a tip port 124 formed in tip 118. The construction of sleeve 116 and tip 118 is substantially as described hereinabove.

Selection of the placement and size of bends 112, 114 and the placement of tip port 124, and the selection of the angle at which tip passageway 122 meets sleeve passageway 120 will determine the degree of maneuverability of I/A needle 102 and give each such instrument an individual, characteristic "feel" to the surgeon.

Sleeves such as those shown at 66 and 90 may be made a permanent part of the instrument or may be inserted over a corresponding I/A needle. The choice of material for sleeves 66, 90 makes tips 68, 92 especially suited for opthalmological work in that such tips are smooth, relatively soft and less likely to cause damage to delicate eye tissue.

I claim:

1. A surgical instrument, said surgical instrument comprising:
    a needle mount having a passageway;
    a needle having a rigid needle body,
    said needle body having a length between proximal and distal ends,
    said proximal end extending from said needle mount,
    said needle body having a passageway extending from said proximal end to said distal end,
    said needle body passageway communicating with said needle mount passageway,
    said needle body passageway terminating at said distal end at a needle shaft end,
    a hollow elastomeric sleeve having a length and a passageway, said elastomeric sleeve being relatively substantially more flexible than said needle body,
    said sleeve passageway sized and shaped to allow said sleeve to fit over said needle shaft end and at least a portion of said needle body so that the sleeve fully surrounds the needle shaft end,
    said sleeve having a sleeve body extending from said needle shaft end terminating at a rounded sleeve tip,
    said sleeve having spaced lengthwise ends; and
    a passageway formed through said sleeve tip whereby said tip passageway, said sleeve passageway, said needle passageway and said mount passageway define a continuous flow path.

2. The surgical instrument as recited in claim 1 wherein the sleeve tip passageway has a center, the needle passageway has a central axis, and at least a portion of the center of said sleeve tip passageway extends in a line that is at an angle to the central axis of said needle passageway.

3. The surgical instrument as recited in claim 1 wherein the sleeve tip has an outlet port and at least a portion of said tip passageway has a center that extends in a curved path adjacent to the outlet port.

4. The surgical instrument as recited in claim 1 wherein at least a portion of said sleeve extending past said needle shaft end has a length that is bent.

5. The surgical instrument as recited in claim 1 wherein at least a portion of said needle body has a length that is bent and at least a portion of said sleeve extending past said needle shaft end has a length that is bent.

6. The surgical instrument as recited in claim 1 wherein said sleeve is formed from silicone.

7. The surgical instrument as recited in claim 1 wherein the sleeve passageway has a length that is non-straight between the spaced ends of the sleeve body.

8. The surgical instrument as recited in claim 1 wherein the needle body is non-straight between the proximal and distal ends of the needle body.

9. The surgical instrument as recited in claim 1 wherein the rounded sleeve tip is spaced a distance from said needle shaft end.

10. The surgical instrument as recited in claim 1 wherein the rounded sleeve tip has a diameter larger than a diameter of the sleeve body.

11. The surgical instrument as recited in claim 1 wherein the sleeve tip is substantially spherical.

12. The surgical instrument as recited in claim 1 wherein the sleeve extends over a majority of the length of the needle body.

13. The surgical instrument as recited in claim 1 wherein the sleeve body having a first length between the needle shaft end and the rounded sleeve tip, the entire first length projecting away from the needle shaft in a proximal to distal direction relative to the needle body length.

* * * * *